United States Patent
Johnson et al.

(10) Patent No.: US 6,826,429 B2
(45) Date of Patent: Nov. 30, 2004

(54) INTERFERENTIAL CURRENT TREATMENT APPARATUS

(75) Inventors: Benjamin Glade Johnson, Layton, UT (US); Donald Alan Rhodes, Corpus Christi, TX (US)

(73) Assignees: Dynatronics Corporation, Salt Lake City, UT (US); Alan Neuromedical Technologies, LLC, Corpus Christi, TX (US)

(*) Notice: Subject to any disclaimer, the term of this patent is extended or adjusted under 35 U.S.C. 154(b) by 179 days.

(21) Appl. No.: 09/765,939

(22) Filed: Jan. 19, 2001

(65) Prior Publication Data

US 2002/0099425 A1 Jul. 25, 2002

(51) Int. Cl.[7] .................................................. A61N 1/36
(52) U.S. Cl. ...................................................... 607/67
(58) Field of Search .............................. 607/66–69, 76, 607/46, 50

(56) References Cited

U.S. PATENT DOCUMENTS

| | | | |
|---|---|---|---|
| 3,774,620 A | * 11/1973 | Hansjurgens | 607/67 |
| 4,023,574 A | * 5/1977 | Nemec | 607/67 |
| 4,153,061 A | * 5/1979 | Nemec | 607/67 |
| 4,280,504 A | * 7/1981 | Rodler | 607/67 |
| 4,538,598 A | 9/1985 | Gill et al. | 128/75 |
| 5,269,304 A | * 12/1993 | Matthews | 607/46 |
| 5,512,057 A | * 4/1996 | Reiss et al. | 607/67 |
| 5,620,481 A | * 4/1997 | Desai et al. | 607/101 |
| 5,776,173 A | * 7/1998 | Madsen, Jr. et al. | 607/67 |
| 5,995,873 A | 11/1999 | Rhodes | 607/46 |
| 6,393,328 B1 | * 5/2002 | McGraw et al. | 607/72 |
| 6,560,487 B1 | * 5/2003 | McGraw et al. | 607/51 |

* cited by examiner

*Primary Examiner*—Kennedy Schaetzle
(74) *Attorney, Agent, or Firm*—Berne S. Broadbent; Kirton & McConkie (57) ABSTRACT

An apparatus for treating patients using electrical interferential therapy is disclosed. The apparatus uses multiple electrodes to define multiple treatment channels, with each channel having a discrete frequency and an adjustable beat frequency between all or selected channel pairs. This adjustment can be done between treatment sessions or can be done during the treatment session by the technician or by the apparatus as programmed. The multiple treatment channels can be used on the same patient, or can be used by the same or a different technician to treat additional patient(s).

10 Claims, 4 Drawing Sheets

INTERFERENTIAL CURRENT TREATMENT APPARATUS

BACKGROUND

The present invention relates generally to the treatment of the human body and, more particularly, to an apparatus that utilizes multiple electrical currents to generate multiple interferential beat patterns to treat one or more patients.

It is well-known in the art to treat a patient experiencing pain or other symptoms using electro-stimulation. Electro-stimulation treatment brings therapeutic benefit by stimulating the nerves and muscles of the patient to rehabilitate injuries to the nerves or muscles and to relieve pain.

Another well known treatment method is electrical interferential therapy. Electrical interferential therapy is performed by establishing electrical circuits within the body of the patient so that the circuits cross and interfere with one another when operating at different frequency levels. Electrodes are placed on selected locations on the patient's body to complete an electrical circuit connecting the two electrode locations. The electrical current is an alternating current and each of the two circuits is operated at a slightly different frequency, which generates a beat frequency within the body where the circuits cross. The beat frequency serves as the interference point that provides the desired therapeutic treatment and benefit.

Some prior electrical interferential treatment devices utilize only two circuits where the first circuit has a fixed base frequency and a fixed second frequency for the second circuit. In some prior art devices, the second frequency may vary or sweep in an increasing or decreasing phase relative to the first frequency, thereby causing the beat frequency to vary or sweep. This use of but two circuits limits treatment to a single patient with a single beat frequency pulse available for treatment. Further still, the base frequency is not adjustable during treatment. This limits the ability of the therapist to customize the treatment for individual patients using specific therapies or protocols.

The prior art has introduced interferential current systems that provide four electrical circuits. The first two circuits are placed to intersect at a first treatment area within body. The second two circuits are placed to intersect at a different area of the body. The systems, however, are limited to using but one base frequency for the two treatment channel pairs. Specifically, the frequency of the first circuit operates at the same frequency of the third circuit. Thus, only beat frequencies between the first and second circuits as well as between the third and fourth circuits are utilized. In addition, the base frequencies may be changed prior to treatment, but they cannot be changed during treatment.

What is lacking, therefore, is an electrical interferential treatment apparatus that allows the operator to select multiple and different base frequencies simultaneously between the treatment channel pairs as well as to adjust or change the frequencies of all circuits during treatment. Further what is needed is an interferential treatment apparatus that is capable of treating more than one patient at a time utilizing multiple and different base frequencies simultaneously. Further still, what is needed is an interferential treatment apparatus that allows the operator to increase the number of interferential treatment effects without necessarily increasing the number of circuits established in the patient(s) by increasing the number of beat frequencies generated between circuits.

SUMMARY OF THE INVENTION

According to the present invention, an apparatus for treating patients using electrical interferential therapy is disclosed. The apparatus utilizes multiple pairs of electrodes to define multiple treatment circuits, with each circuit operating at a discrete base frequency and an adjustable beat frequency between all or selected circuit pairs. The frequency adjustment can be done between treatment sessions or can be done during the treatment session by the technician or by the apparatus as programmed prior to the start of the treatment session. The multiple treatment circuits can be used on the same patient, or can be used by the same or a different technician to treat at least one additional patient.

The apparatus includes a plurality of electrical circuits, which define treatment channels. Each circuit or channel includes a pair of electrodes that are placed strategically on the patient. Electrical circuits are generated between electrode pairs to form each treatment channel. The electrodes are placed on sides opposite the patient's spine for optimal treatment. For example, one electrode is placed on the patient's foot and the corresponding electrode on the opposite foot. The electrode on the opposite side can be placed on the hand, shoulder, hip, or other region of the body, so long as it is on the opposite side of the first electrode along a known nerve path between the electrode contact points thereby establishing a current path through the patient's spine. Each electrical circuit channel carries an alternating current generated by a current source device within the treatment apparatus. The current source device is capable of providing multiple electrical currents, one for each desired circuit. The frequency of each circuit can be varied and a plurality of beat pulses can be generated based upon the placement of the electrodes used to form the plurality of circuits. The circuits can have a cumulative effect on a particular spinal nerve region or serve a plurality of nerve regions adjacent to one another based upon the needs of the patient. The current source device, in one embodiment, utilizes various elements, which include a digital signal processor (DSP), coupled to a central processing unit (CPU) and a digital-to-analog converter (DAC). The CPU is programmed so that each frequency for each circuit can be varied. Further, the DSP receives direction from the CPU to set the frequency for each circuit, which utilizes the DAC to convert the digital signal to an analog signal for the alternating current of each circuit.

BRIEF DESCRIPTION OF THE DRAWINGS

The foregoing and other objects and features of the present invention will become more fully apparent from the following description and appended claims, taken in conjunction with the accompanying drawings. Understanding that these drawings depict specific embodiments of the invention and are, therefore, not to be considered limiting of its scope, the invention will be described and explained with additional specificity and detail through the use of the accompanying drawings in which:

DETAILED DESCRIPTION OF SPECIFIC EMBODIMENTS

It will be readily understood that the components of the present invention, as generally described and illustrated in the figures herein, could be arranged and designed in a wide variety of different configurations. Thus, the following more detailed description of the embodiments of the system and method of the present invention, and represented in FIGS. 1–5, is not intended to limit the scope of the invention, as claimed, but is merely representative of embodiments of the invention.

The specific embodiments of the invention will be best understood by reference to the drawings, wherein like parts are designated by like numerals throughout.

In the practice of this invention, electric circuits are established in the body of a patient. Each circuit utilizes two electrical contact points, such as electrodes, placed strategically on the body. Generally, four such circuits are established through the body via four pairs of contact points. Each electric circuit is placed across nerve fibers having one terminus on an extremity, i.e. on the foot or hand of the patient, and one terminus adjacent a sympathetic nerve ganglia near a nerve ganglia adjacent a particular vertebra in the spinal column. Some type of electrical connection, but the exact details of which are not limiting, is made between the nerve ganglia adjacent the spinal column. It is clear that the circuit includes the nerve fibers that extend from the more distal aspect of a first peripheral nerve to its root adjacent the spinal column. It is believed the circuit continues through the root of the first nerve into the spinal column, through the spinal column and exits from the spinal column through the root of a second nerve. The circuit continues through the fibers of the second peripheral nerve to a more distal aspect of that nerve.

Figures 1, 2:
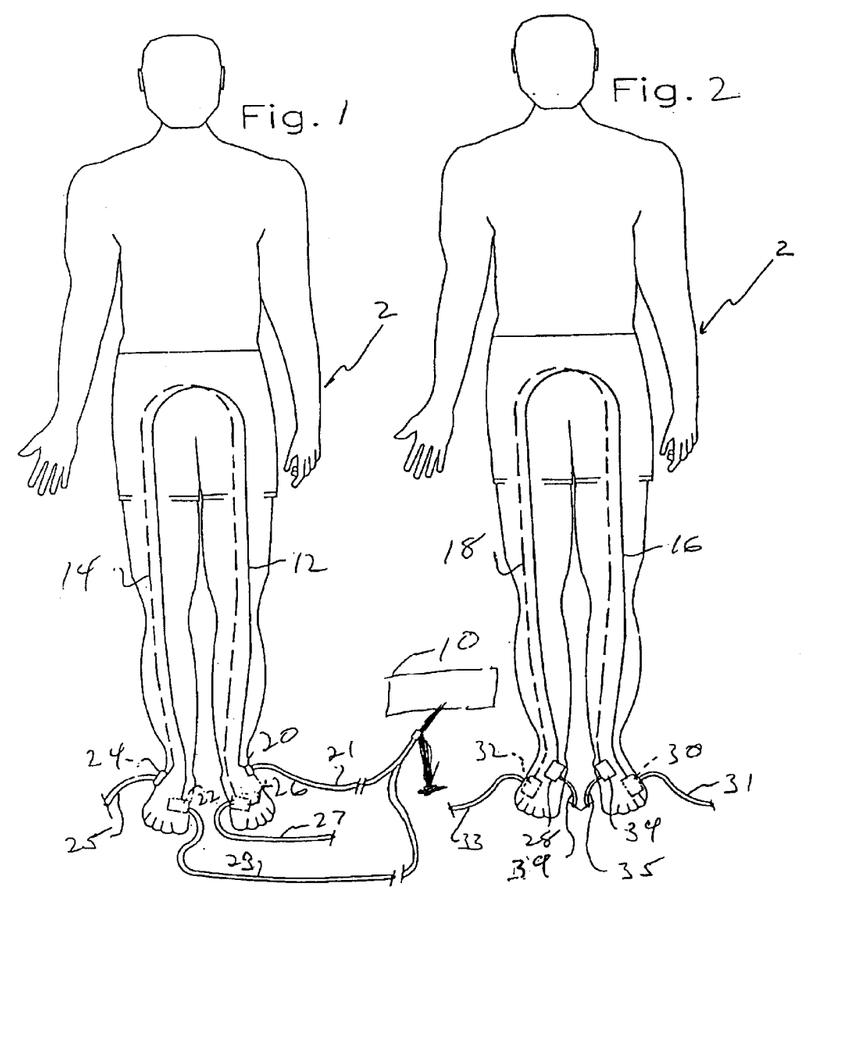
FIGS. 1 and 2 illustrate the electrical interferential therapy apparatus in use with a patient in accordance with the present invention.

FIGS. 1 and 2 illustrate a variable frequency interferential current treatment apparatus 10 used during the treatment of a patient 2 in accordance with the present invention. Apparatus 10 includes a plurality of electrical treatment channels 12, 14, 16, and 18, which are utilized to apply an electrical current and establish an electrical circuit on patient 2 via attachment electrodes. The use of multiple figures aids in the clarity of the channel and electrode locations, which would otherwise be cluttered if placed in a single figure. Thus, FIGS. 1 and 2 are intended to represent the same patient 2, but they can also illustrate multiple patients receiving treatment with the same number of electrodes, i.e. 8 electrodes. It will be better understood as described below why four channels are desired in accordance with the specific embodiments of the present invention.

A first electrical circuit is established by placing a first electrode 20 at a first location on a patient and a second electrode 22 at a second location on the patient. The electrodes are further connected to electrical leads 21 and 23, respectively, which are further connected to apparatus 10. Electrical leads 21 and 23 serve to apply a voltage difference across the electrodes, thereby generating a treatment current within the body of the patient. In one embodiment, the locations are opposite one another relative to the spinal cord of the patient so that the electrical circuit interacts with and stimulates the spinal cord. A second circuit can be established on the patient by placing a third electrode 24 at a third location on the patient and a fourth electrode 26 at a fourth location on the patient. The electrodes are further connected to electrical leads 25 and 27, respectively, which are further connected to apparatus 10. Electrical leads 25 and 27 serve to apply a voltage difference across the electrodes, thereby generating a second treatment current within the body of the patient. Again, the location of the third and fourth electrodes are on opposite sides of the spinal cord of the patient so that the electrical stimulation interacts with the spinal cord. U.S. Pat. No. 5,995,873, issued Nov. 30, 1999 to Rhodes, incorporated by reference for all purposes, teaches a method of treating a patient using interferential currents. The treatment methods for placement and stimulation of the spine as taught in U.S. Pat. No. 5,995,873 provide one specific embodiment of the electrode placement and nerve stimulation using interferential currents in accordance with present invention.

The electrodes 20, 22 are attached to the patient's skin in a conventional manner, i.e. they are self adherent or are taped in place. The location of the electrodes 20, 22 on the patient establish the electrical circuit in the patient's body. As shown in FIG. 1, in one technique, one electrode 22 is placed adjacent the end or terminus of the right medial plantar nerve L5 and its matching electrode 20 is placed adjacent the end or terminus of the left sural nerve S1, inferior to the left ankle bone (lateral malleolus) thereby establishing or creating a first circuit 12 in the patient's body. As used herein, the reference characters L5, S1 and the like are standard medical terminology for the nerve. Those skilled in the art will recognize L5 as being the nerve which extends away from the fifth lumbar vertebra and S1 as being the nerve which extends away from the first sacral vertebra.

Those skilled in the art will recognize that the terminus of the right medial plantar nerve L5 is located on the bottom of the right foot approximately on the ball of the foot. The terminus of the left sural nerve S1 is located below the left ankle bone (lateral malleolus). Another electrode 24 is placed adjacent the terminus of the right sural nerve S1 and its matching electrode or mate 26 is placed adjacent the terminus of the left medial plantar nerve L5 thereby establishing a second circuit 14 in the patient's body. Apparatus 10 delivers electrical energy through circuits 12, 14. Experience has shown a decrease in pain in patients complaining of pain and a decrease in symptoms consistent with an imbalanced sympathetic nervous system. Those skilled in the art will recognize that the medial plantar nerves L5 and the sural nerves S1 terminate adjacent the spinal column near adjacent spinal vertebra, in the area of the connection to the lumbar sympathetic ganglia.

As shown in FIG. 2, the electrode 32 is attached to the skin of the patient adjacent the terminus of the right lateral plantar nerve L5 and its matching electrode or mate 34 is placed adjacent the terminus of the left saphenous nerve L4, at the ankle, thereby establishing a circuit 18 Those skilled in the art will recognize that the terminus of the right lateral plantar nerve L5 is on the bottom of the right foot below the little toe and the fourth toe on the pad of the foot near the fifth metatarsal head. The terminus of the left saphenous nerve L4 is on the top inside (medial-anterior aspect) of the left ankle. Electrodes 32 and 34 are further connected to electrical leads 33 and 35, respectively, which are further connected to apparatus 10. Electrical leads 33 and 35 serve to apply a voltage difference across the electrodes, thereby generating a third treatment current within the body of the patient.

An electrode 28 is attached to the surface of the skin of patient 2 adjacent the terminus of the right saphenous nerve L4 and its matching electrode or mate 30 is placed adjacent the terminus of the left lateral plantar nerve L5 thereby establishing a circuit 16. Those skilled in the art will recognize that the terminus of the right saphenous nerve L4 is on the top inside of the right foot, forward of the right ankle and that the lateral plantar nerve L5 and the saphenous nerve L4 terminate adjacent the spinal column near adjacent spinal vertebrae. The terminus of the left lateral plantar nerve is on the bottom of the left foot below the little toe and the fourth toe on the pad of the foot. Electrodes 28 and 30 are further connected to electrical leads 29 and 31, respectively, which are further connected to apparatus 10. Electrical leads 29 and 31 serve to apply a voltage difference from apparatus 10 across the electrodes, thereby generating a fourth treatment current within the body of patient 2.

The electrical current provided for each circuit 12, 14, 16, 18 interfere with one another achieving interferential treatment beneficial to the patient. Patients have indicated reduction of pain and symptoms that are consistent with a dysfunction of the sympathetic nervous system, including nerve pain, diaphoresis, decreased peripheral circulation, high blood pressure, and inflammation, among others. The techniques of FIGS. 1 and 2 are run simultaneously with separate settings for base frequency and beat frequency via apparatus 10.

The circuits cross paths or share a common nerve span within the spinal column of patient 2. These nerve spans are shown in greater detail in FIG. 3, where the circuits or channels are depicted as they cross one another. Channel 12 passes through a peripheral nerve at the S1 level and exits the L5 level on the opposite side of the body. Channel 14 enters through a peripheral nerve at the L5 level. It exits the S1 level on the opposite side of the body. Channel 16 enters through a peripheral nerve at the L5 level and exits the L4 level on the opposite side of the body. Channel 18 enters through a peripheral nerve at the L4 level and exits the L5 level on the opposite side of the body.

Figure 3:
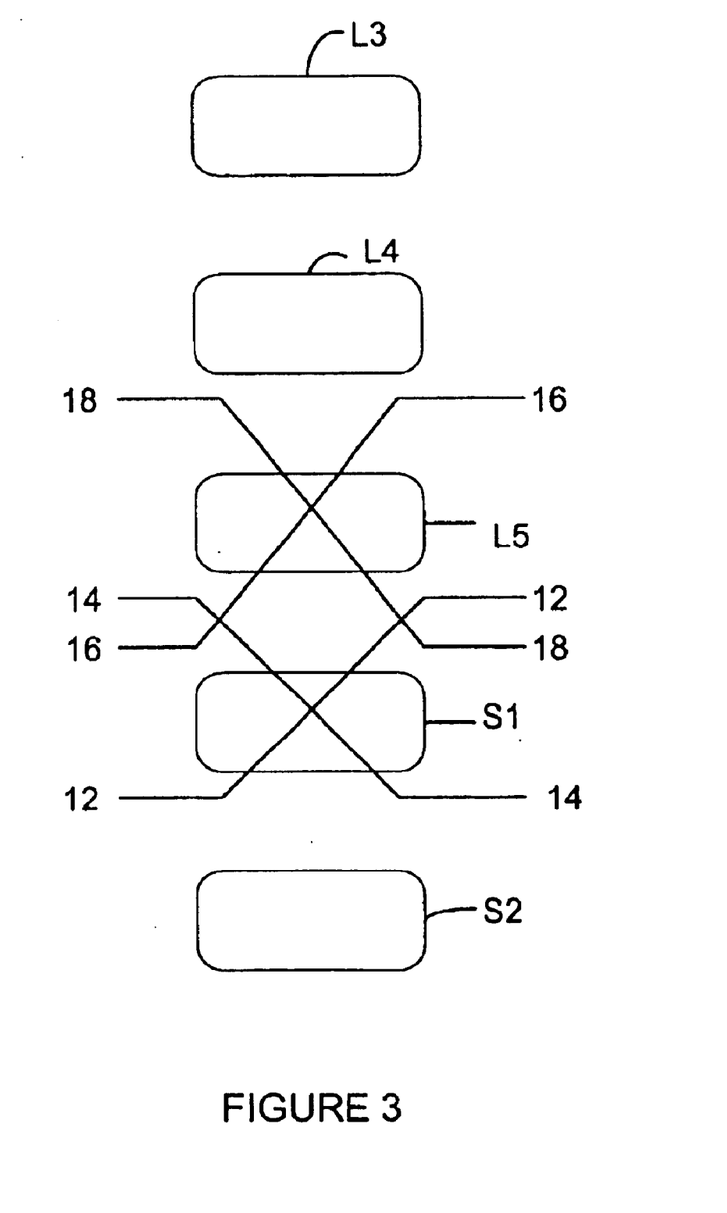
FIG. 3 illustrates the circuit paths through the spine in accordance with the electrode locations of FIGS. 1 and 2.

Although FIG. 3 illustrates that the circuits or channels cross paths, it is not necessary that the paths actually cross, but merely share the same nerve path or level such as, for example, sharing L5 or S1. Other arrangements of the electrodes placed on selected extremities or shoulders to stimulate other nerves are within the scope of this invention. For example, locations on one extremity such as the hand to another extremity are known to be connected via a nerve path with either the opposite hand or the opposite foot or leg.

It is also illustrated that multiple circuits, in this example, all four circuits, can be layered upon the same nerve level, for example L5, to provide enhanced treatment of the nerve level believed needing the most attention for pain or symptom relief. It is contemplated that three or more circuits can be layered upon the same nerve level for enhanced treatment of the patient. This allows additional beat pulses to treat the affected area, thereby increasing relief in intensity, duration, and more quickly over that of prior art solutions.

Figure 4:
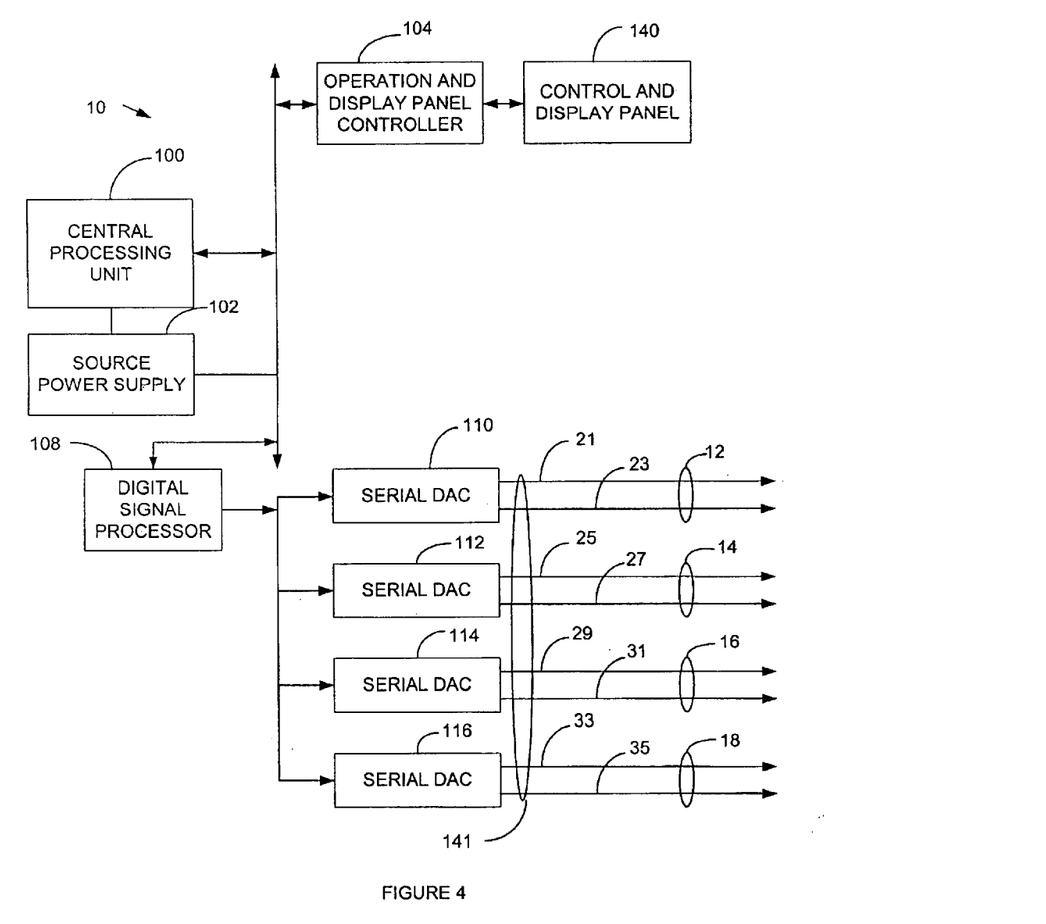
FIG. 4 illustrates a schematic view of the apparatus of FIG. 1.

Interferential treatment apparatus 10 is depicted in greater detail in the schematic diagram of FIG. 4. Treatment apparatus 10 includes a central processing unit 100, which processes inputs from the operator made via a control panel and controls the circuit current, frequency, intensity, and length of time each circuit is active for treatment. CPU 100 is programmed to provide standard operating ranges for interferential current treatment in accordance with the present invention.

Apparatus 10 further comprises a power control or supply unit 102, which is coupled to CPU 100. Power supply unit 102 provides power to apparatus 10 to drive each of the circuits during treatment. Further, power is provided from power supply 102 to power all other elements within apparatus 10 such as control and display panel 140 and CPU 100. CPU 100 controls power supply 102 to determine how much current is provided to each circuit, at what frequency the current operates, and whether the frequency varies during treatment. In one embodiment, power supply 102 manages current from a source, such as an electrical power outlet in the treatment room, to supply multiple currents to the multiple electrode pairs. This source is alternating current with a set frequency, typically 60 Hz, and generally having a voltage level of 110, 120, 210, 220, or 440 volts. Power supply 102 includes appropriate circuitry typically found in a conventional power supply for a treatment apparatus known to one skilled in the art. The power supply stages the current from the original source to each treatment circuit in a conventional manner well known to those skilled in the art.

In an alternative embodiment, power supply 102 utilizes a battery source, such as a 9- or 12-volt rechargeable batter, with appropriate current control and power management circuitry to provide a treatment apparatus 10 that is portable.

Apparatus 10 also includes the plurality of electrical leads 21, 23, 25, 27, 29, 31, 33, and 35 of FIGS. 1 and 2, which are paired together as previously described above to deliver the treatment current for the defined channels. Leads 21, 23, 25, 27, 29, 31, 33, and 35 typically are copper wires, or other suitably conductive material, sheathed in an electrically insulating housing. Leads 21, 23, 25, 27, 29, 31, 33, and 35 can be bundled together as a first electric lead connector 141, also shown in FIG. 5, which provides for easy connection or disconnection of the plurality of leads in a single connector harness. Eight additional leads (not shown), much like leads 21, 23, 25, 27, 29, 31, and 35 can connect to apparatus 10 via a second electric lead connector 145, also shown in FIG. 5.

Apparatus 10 further incorporates isolation transformers, which are well known to those skilled in the art, to stage the power from one voltage level to another as well as to reduce the current output to the patient during treatment. This provides safety to the patient during treatment by isolating the current from the wall source and limiting the current to levels safely accepted in human treatment applications. Specifically, apparatus 10 is designed to limit the electrical current for each treatment circuit to 50 milliamps or less so as to prevent any harmful effects on the patient during treatment. CPU 100 is programmed to regulate the current and voltage to prevent overstimulation or to prevent applying too great a current or voltage during a treatment session.

CPU 100 is further coupled to an operation and display panel controller 104. Controller 104 is further connected to control and display panel 140, which is described in greater detail below with reference to FIG. 5. Controller 104 is programmed to control the operation of control and display panel 140. This enables the operator to select a particular set of patient leads for operation as well as establish the base frequency and the variation set points about that base frequency. When the operator makes a selection through control panel 140, controller 104 converts the operator's selection into signals that can be read and acted upon by CPU 100. CPU 100 then sends out signals consistent with the operator's selection to modify the frequency, current intensity, treatment time length, etc.

Apparatus 10 also incorporates a digital signal processor (DSP) 108, which is further coupled to CPU 100 and to wires 21, 23, 25, 27, 29, 31, 33, and 35. DSP 108 receives signals from CPU 100 directing it drive each electrical circuit at the frequency selected by the operator or that is set as a default frequency. Thus, when the operator selects 1850 Hz as the frequency for circuit 12, signals are sent from controller 104 to CPU 100, which then sends a signal to DSP 108, thereby causing circuit 12 operate at the selected frequency. Apparatus 10 also incorporates a digital to analog convertor, for example, digital to analog convertor (DAC) 110 for the conductor wire pairs 21, 23 that form circuit 12. Each circuit has its own DAC. Thus a second DAC 112 is also connected to DSP 108 and conductor wire pairs 25, 27 for second channel 14. Third DAC 114 is connected to DSP 108 and to conductor wire pairs 29, 31 for third channel 16. Fourth DAC 116 is connected to DSP 108 and to conductor wire pairs 33, 35 for fourth channel 18. Additional wire pairs and DACs are typically provided for additional circuits, which are grouped in fours for interferential treatment consistent with the present invention.

The wire pairs can be color coded, as indicated by the R, W, Y, and B, representing red, white, yellow, and black, respectively, on the window of selector 148. Thus, during treatment setup, if the apparatus detects poor conductivity for any channel, the corresponding initial (R, W, Y or B) is highlighted and an error code displayed. The operator then checks the lead for contact with the patient or connection with the apparatus, or whether it is defective and should be replaced before treatment can begin.

Figure 5:
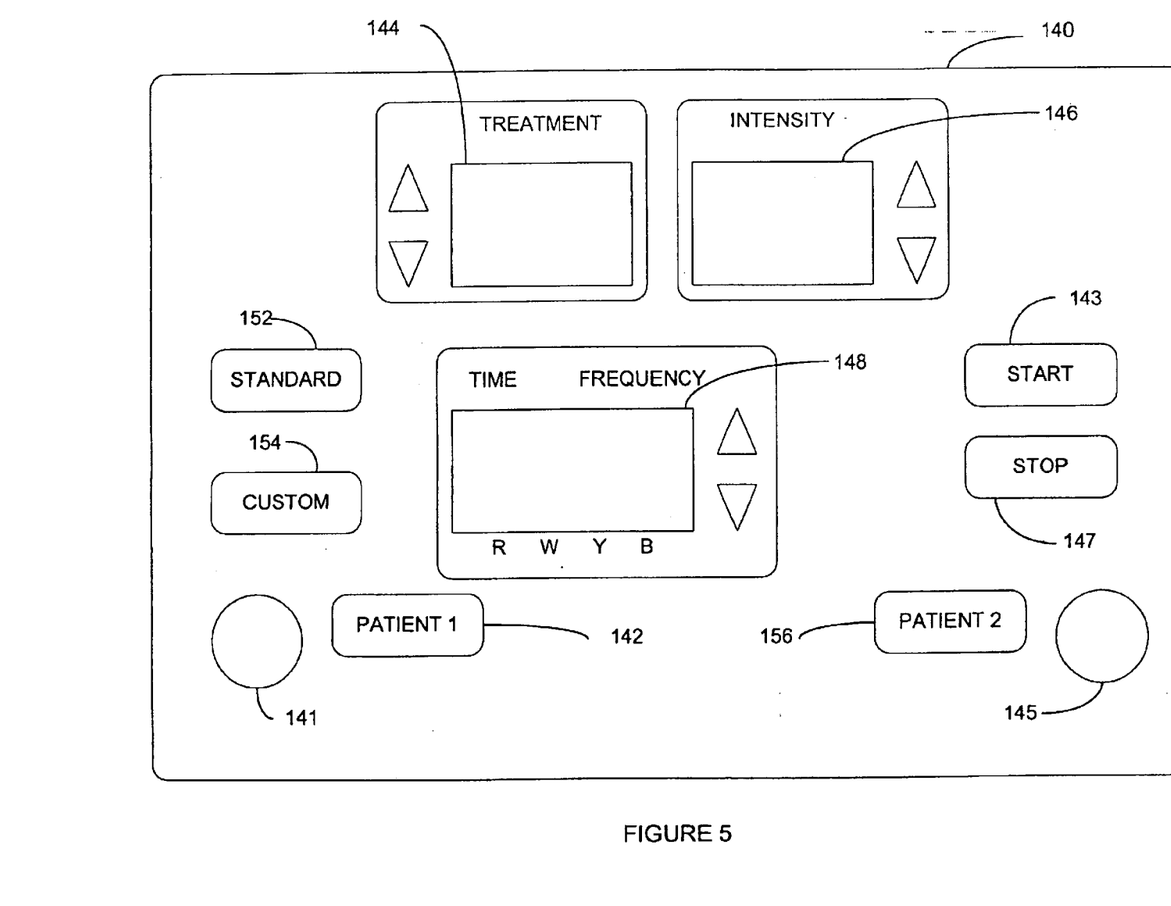
FIG. 5 illustrates the control panel of the apparatus of FIG. 4.

FIG. 5 illustrates in greater detail control panel 140 of FIG. 4. Selector 142 allows the operator to program apparatus 10 for treatment of a first patient, which includes selecting the treatment type through treatment selector 144, selecting the intensity of the treatment current(s) through intensity selector 146, and selecting the time needed for treatment through time selector 148. Time selector 148 has multiple functions as selected through various key presses. The key presses enable the user to set the beat frequency or the base frequency, or both. In alternative embodiments, both the beat frequency and the base frequency can be selected via dedicated switches as opposed to the multi-function switch of FIG. 5.

Other features available to the operator include a standard setting switch 152 and a custom setting switch 154. Standard setting switch 152 enables the operator to select a default or standard treatment regimen of a preset length of time, preset beat frequency, and a preset beat frequency. The treatment intensity, or current strength, is determined by the operator during treatment based on the needs of the patient. Custom setting switch 154 enables the operator to customize treatment regimens for particular treatment effects. For example, the operator may want to vary the beat frequency during the treatment. Once a treatment session has been setup, the operator begins the treatment session by activating start switch 143, which starts the treatment timer to count down the treatment session. Current flow through each circuit at the selected frequency begins when the selected intensity is made. Further, a stop switch 147 is also provided that serves to stop all functions of apparatus 10 during a treatment session. This enables the patient or operator to stop the treatment session, such as the current flow, immediately for any reason.

When another patient is treated, the operator selects second patient selector 156 before programing apparatus 10 for the second treatment session. The circuit frequencies, beat frequencies, treatment times, and current intensity are controlled in the same manner as that described for selector 142, independently and without interfering with the treatment session of the first patient.

One embodiment of control panel 140 utilizes a 7-segment LED display for each display field. Alternative embodiments can include, but are not limited to, LCD displays, CRT displays, or analog displays. Touch screen displays or touch pads that provide scroll through menu selection or alpha-numeric, or both, are also contemplated within the present invention.

In alternate embodiments, separate displays can also be provided for each patient or the system can use a single display and display information alternating between multiple patients, as selected using the control panel 140.

To establish the first interferential circuit, two electrical circuits are established that operate at different frequencies from one another. Thus, where the first interferential circuit comprises circuit 12 and circuit 14, the base frequency for circuit 12 is 1850 Hz, which can be selected by the operator or set as a default frequency for each treatment session. Other frequencies are selectable for circuit 12. The second frequency, which applies to second channel 14, is selected to be different than that of the first base frequency, but in one embodiment the second frequency is intended to be within 200 Hz of the base frequency. Thus, the difference would be 200 Hz or less, which establishes a beat difference or frequency of 200 Hz or less used in therapeutic treatment.

A second interferential current circuit is established in the same patient utilizing third circuit 16 and fourth circuit 18. The electrodes for circuit 16 are placed in opposite locations relative to the spine of the patient, for example, as shown in FIG. 2. The base frequency for circuit 16 is typically selected to be at least 500 Hz greater than that of circuit 12 and is commonly selected to be 1000 Hz greater, which is 2850 Hz when circuit 12 is set at 1850 Hz. This selection is performed by the operator or is preset automatically by apparatus 10. Next, the base frequency for circuit 18 is selected to set a difference between circuits 16 and 18 of 200 Hz or less. This produces a beat frequency between the two circuits of 200 Hz.

In selected embodiments, the beat frequency has a range of 2 to 6 Hz, but is not to be limiting. Other base frequencies are possible and the 1850 Hz and 2850 Hz base frequencies are provided by way of example. The upper limit on the base frequency has not been determined, but frequencies as high as 10,000 Hz are acceptable as are beat frequencies as high as or in excess of 1000 Hz and as low as 1 Hz. In one specific embodiment, apparatus 10 controls the beat frequency to sweep between a selected range of a first value and a second value where the first value is the upper limit and the second value being as low as zero, which means the second frequency would be equal to the first frequency during this sweep operation.

When the electrical current treatment circuits are placed to overlap one another in one spinal nerve level or share the same spinal nerve level, other beat frequencies are possible and encouraged as it has been determined that the additional beat pulses produced by the additional beat frequencies provide therapeutic benefits of reduced pain or discomfort. Specifically, when channel 12 and 16 have respective frequencies of 1850 and 2850, a third beat frequency of 1,000 Hz occurs, which provides a beat pulse of 1,000 Hz. Before, it was thought that such a high frequency differential between the two channel pairs caused no overlap, but for reasons not fully understood, this high frequency beat difference has been observed to provide enhanced therapeutic effects in addition to the therapeutic effects of the first two defined, lower beat frequencies. Further still, the interference point can be moved about in a treatment area utilizing target technology, as described in U.S. Pat. No. 4,848,347, incorporated by reference for all purposes, in sweep mode.

Thus, additional beat frequencies are produced for each electrical channel that has a frequency different than that of the other channels. It is understood that these beat frequencies are observed only when the circuits overlap another circuit or share a common spinal nerve ganglia or root via the lumbar or cervical paths. The lower beat frequencies have an impact on the autonomic nerve path that provides therapeutic relief and benefit in a manner not clearly understood, but well observed in patient response. Also not well understood, but observed, is that the higher frequency beat frequencies have also been found to have an impact on the autonomic nerve paths adjacent or within the specific nerve paths selected. This brings therapeutic effect to the treated patient. It has been observed that patients who have used the treatments described within the present invention have had success in alleviating or reducing pain not otherwise achieved though conventional treatments or therapies.

Apparatus 10 also allows the treatment of a second patient. Control panel 140 enables the operator to select the set points for each channel to be utilized in the second patient. Control panel 140 enables the operator to treat multiple patients as channels are established via conductors connected to apparatus 10 through port 141 or 145, which transmit electrical current through wires connected to the various electrodes as previously described with respect to FIGS. 1–4. The current provides electrical stimulation via a circuit path established by the electrodes described above. The conductors typically are insulated wires that are either discretely connected to apparatus 10 or the conductors may be bundled together and connected in a universal connector that provides current for each pair of wires used to form a circuit.

In yet another embodiment of the present invention, the first channel can have a fixed base frequency and the second channel has a frequency differential that is either fixed or varied, or pauses at a given frequency relative to the base frequency and can then vary much like the sweep previously mentioned. Likewise, the third channel has a fixed base frequency, different from the first channel pair, with the fourth channel having a frequency differential that is static or varies relative to the frequency of the third channel like that of the frequency of the second channel, but at a frequency different than that of the second channel.

Apparatus 10 can be preprogrammed for treatment as previously mentioned. The following is are a select number of standard presets that can be implemented. A first preset automatically sets two frequency ranges which are applied to both channel pairs at once and are delivered alternately in time segments of 30 seconds each throughout the treatment. In the first preset, the lower beat frequency range is 2 Hz to 6 Hz, the upper beat frequency range is 12 Hz to 18 Hz, and the treatment time is 40 minutes. A second preset uses the same beat frequency ranges as the first preset, but limits the time to 20 minutes.

A third preset automatically sets and applies two frequency ranges in the same way as described for the first preset. In the third preset, however, the lower beat frequency range is 26 Hz to 34 Hz, the upper beat frequency range is 36 Hz to 44 Hz, and the treatment time is 40 minutes. A fourth preset uses the same frequency range presets of the third preset, but limits the treatment time to 20 minutes. A fifth preset automatically sets and applies two beat frequency ranges in the same way as described for the first preset. In the fifth preset, however, the lower beat frequency range is 76 Hz to 84 Hz, the upper beat frequency range is 86 Hz to 94 Hz, and the treatment time is 40 minutes. A sixth preset uses the same beat frequency ranges as found in the fifth preset, but limits the treatment time to 20 minutes.

A seventh preset sets the beat frequency range for the first channel pair at 2 Hz to 6 Hz, the second channel pair has a beat frequency range of 8 Hz to 12 Hz, and the treatment time at 40 minutes. An eighth preset uses the same beat frequency settings as those of the seventh preset, but sets the treatment time to 20 minutes. In specific applications, it has been observed that the beat frequency settings used in the seventh and eighth result in greater therapeutic relief and benefit to patients over those previously described, but that the others do provide useful and beneficial results as well.

The present invention may be embodied in other specific forms without departing from its spirit or essential characteristics. The described embodiments are to be considered in all respects only as illustrative and not restrictive. For example other frequency ranges can be used aside from those specifically mentioned and other presets are possible as the listed ones. The scope of the invention is, therefore, indicated by the appended claims, rather than by the foregoing description. All changes which come within the meaning and range of equivalency of the claims are to be embraced within their scope.

What is claimed is:

1. An interferential current treatment apparatus comprising:

a first electrical circuit having a first current source, a first variable base frequency, and a first pair of treatment electrodes, wherein the first pair of treatment electrodes are configured for selective coupling to opposing sides of a patient's body with respect to a spinal column of the patient to allow the first electrical circuit to interact with and stimulate a nerve span of the patient's spinal column;

a second electrical circuit having a second current source, a second variable base frequency, and a second pair of treatment electrodes, wherein the second pair of treatment electrodes are configured for selective coupling to opposing sides of the patient's body with respect to the spinal column of the patient to allow the second electrical circuit to interact with and stimulate the nerve span of the patient's spinal column, and wherein the second base frequency is within 200 Hertz of the first base frequency when attached to the patient, wherein a first interferential beat frequency is established between the first and second electrical circuits;

a third electrical circuit having a third current source, a third variable base frequency, and a third pair of treatment electrodes, wherein the third pair of treatment electrodes are configured for selective coupling to opposing sides of the patient's body with respect to the spinal column of the patient to allow the third electrical circuit to interact with and stimulate the nerve span of the patient's spinal column, and wherein the third base frequency is greater than the first base frequency by at least 500 Hz when attached to the patient; and a fourth electrical circuit having a fourth current source, a fourth variable base frequency, and a fourth beat frequency, and a fourth pair of treatment electrodes, wherein the fourth pair of treatment electrodes are configured for selective coupling to opposing sides of the patient's body with respect to the spinal column of the patient to allow the fourth electrical circuit to interact with and stimulate the nerve span of the patient's spinal column, and wherein the fourth base frequency is no more than 200 Hertz greater than the third base frequency when attached to a patient, wherein a second interferential beat frequency is established between the third and fourth electrical circuits.

2. The apparatus according to claim 1 further comprising frequency varying means coupled to the first, second, third and fourth current sources to vary a beat frequency of at least one of the electrical circuits relative to another of the electrical circuits during use.

3. The apparatus according to claim 2 wherein a frequency varying means selectively varies the beat frequency either before treatment or during treatment of the patient.

4. The apparatus according to claim 1 wherein the first inferential beat frequency is 2–6 Hz.

5. The apparatus according to claim 4 wherein the second inferential beat frequency is 8–12 Hz.

6. The apparatus according to claim 1 wherein the first base frequency is set generally at 1850 Hertz.

7. The apparatus according to claim 1 further comprising means for displaying the frequencies and elapsed time of use of each of the current sources.

8. The apparatus according to claim 1 wherein an interferential beat frequency is established between the first electrical circuit and the third electrical circuit.

9. The apparatus according to claim 1 wherein at least some of the current sources are alternating current sources and a signal generator applies a frequency on the alternating current of the alternating current sources.

10. The apparatus according to claim 9 further comprising display and control means, coupled to the signal generator, to enable an operator to control a current level and frequency of each current source and to display the same to the operator.

* * * * *